United States Patent [19]

L'Esperance, Jr.

[11] Patent Number: 4,770,172

[45] Date of Patent: * Sep. 13, 1988

[54] METHOD OF LASER-SCULPTURE OF THE OPTICALLY USED PORTION OF THE CORNEA

[75] Inventor: Francis A. L'Esperance, Jr., Englewood, N.J.

[73] Assignee: LRI L.P., New York, N.Y.

[*] Notice: The portion of the term of this patent subsequent to May 19, 2004 has been disclaimed.

[21] Appl. No.: 49,333

[22] Filed: May 13, 1987

Related U.S. Application Data

[63] Continuation-in-part of Ser. No. 748,358, Jun. 24, 1985, Pat. No. 4,665,913, Ser. No. 891,169, Jul. 31, 1986, Pat. No. 4,729,372, and Ser. No. 891,285, Jul. 31, 1986, Pat. No. 4,732,148, said Ser. No. 748,358, is a continuation-in-part of Ser. No. 552,983, Nov. 17, 1983, abandoned, said Ser. No. 891,169, is a continuation-in-part of Ser. No. 780,335, Sep. 26, 1985, abandoned, which is a continuation-in-part of Ser. No. 740,276, Jun. 3, 1985, abandoned, which is a continuation of Ser. No. 552,983, , said Ser. No. 891,285, is a continuation-in-part of Ser. No. 778,801, Sep. 23, 1985, abandoned, which is a continuation-in-part of Ser. No. 742,225, Jun. 6, 1985, abandoned, which is a continuation-in-part of Ser. No. 552,983.

[51] Int. Cl.$^4$ ............................................. A61F 9/00
[52] U.S. Cl. .................................. 128/303.1; 128/395
[58] Field of Search ................... 128/303.1, 362, 395, 128/397, 398

[56] References Cited

U.S. PATENT DOCUMENTS 4,665,913 5/1987 L'Esperance .................. 128/303.1

Primary Examiner—William E. Kamm
Assistant Examiner—David Shay
Attorney, Agent, or Firm—Hopgood, Calimafde, Kalil, Blaustein & Judlowe

[57] ABSTRACT

The invention contemplates removal of epithelium-layer material from the anterior surface of the cornea, as a step preparatory to laser surgery, wherein controlled ultraviolet irradiation of the cornea is operative to surgically ablate corneal tissue within an epithelium-free area which is in the optically used central region of the cornea; the control is such as to effect a predetermined sculpted corrective-curvature change in the optically used region. Other important pre-surgery and post-surgery procedural steps are disclosed, for greater assurance of a predictable curvature change through the sculpting laser surgery.

19 Claims, 1 Drawing Sheet

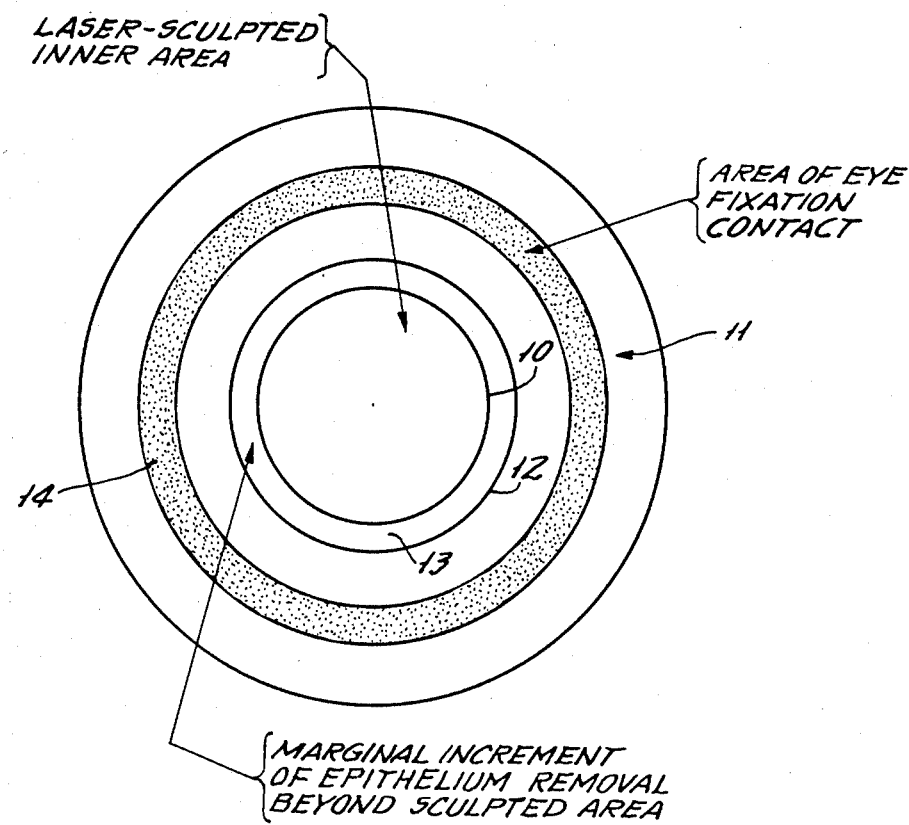

METHOD OF LASER-SCULPTURE OF THE OPTICALLY USED PORTION OF THE CORNEA

RELATED CASES

This application is a continuation-in-part of pending applications Ser. No. 748,358, filed June 24, 1985, now U.S. Pat. No. 4,665,913, Ser. No. 891,169, filed July 31, 1986, now U.S. Pat. No. 4,729,372 and Ser. No. 891,285, filed July 31, 1986, now U.S. Pat. No. 4,732,148. Said application Ser. No. 748,358 is a continuation-in-part of original application Ser. No. 552,983, filed Nov. 17, 1983 (now abandoned). Said application Ser. No. 891,169 is a continuation-in-part of application Ser. No. 780,335, filed Sept. 26, 1985 (now abandoned); said application Ser. No. 780,335 is a continuation-in-part of application Ser. No. 740,276, filed June 3, 1985 (now abandoned); and said application Ser. No. 740,276 is a continuation of said original application. Said application Ser. No. 891,285 is a continuation-in-part of application Ser. No. 778,801, filed Sept. 23, 1985 (now abandoned); said application Ser. No. 778,801 is a continuation-in-part of application Ser. No. 742,225 (now abandoned); and said application Ser. No. 742,225 is a continuation-in-part of said original application. The disclosures of said applications are incorporated herein by reference.

BACKGROUND OF THE INVENTION

The invention relates to that aspect of ophthalmic surgery which is concerned with operations upon the external surface of the cornea.

Operations of the character indicated include corneal transplants and keratotomies; such operations have traditionally required skilled manipulation of a cutting instrument. But, however keen the cutting edge, the mere entry of the edge into the surface of the cornea necessarily means a wedge-like lateral pressure against body cells displaced by the entry, on both sides of the entry. Such lateral pressure is damaging to several layers of cells on both sides of the entry, to the extent impairing the ability of the wound to heal, and resulting in the formation of scar tissue.

My original patent application Ser. No. 552,983, filed Nov. 17, 1983, includes a background discussion of the effects of various available wavelengths of laser radiation in ophthalmic surgery and, in particular, surgery performed on the anterior surface of the cornea. It is explained that radiation at ultraviolet wavelengths is desirable by reason of its high photon energy. This energy is greatly effective on impact with tissue, in that molecules of tissue are decomposed on photon impact, resulting in tissue ablation by photodecomposition. Molecules at the irradiated surface are broken into smaller volatile fragments without heating the remaining substrate; the mechanism of the ablation is photochemical, i.e., the direct breakdown of intra-molecular bonds. Photothermal and/or photocoagulation effects are neither characteristic nor observable in ablations at ultraviolet wavelengths, and cell damage adjacent the ablation is insignificant.

Said related-case applications deal with various concepts whereby laser radiation at ultraviolet wavelengths of 200-nm or less are controlled in delivery of laser radiation to the visually used area of the anterior surface of the cornea so as to penetrate the stroma and achieve a predeterminable volumetric removal of corneal tissue, thereby so correctively changing the profile of the anterior surface as to reduce a myopia, or a hyperopia, or an astigmatic abnormality which existed prior to such laser surgery.

Said related-case applications were concerned primarily with the methods and means of achieving desired corneal sculpture through controlled delivery of ultraviolet laser radiation. The disclosures of these applications were addressed to ophthalmic surgeons who presumably are skilled in traditional procedures; but, although the laser-sculpting procedures I disclosed were contrary to current professional practice and beliefs, in the sense that I called for ablation depths which necessarily involved traversing Bowman's membrane in order to penetrate the stroma, I have been surprised that those skilled in laser technology who would attempt to experimentally apply my disclosures to their own research, have been unduly preoccupied with the epithelium, namely, the thin regrowable layer which nature provides for protection of the anterior surface of the cornea. I have found that such preoccupation with the epithelium can not only produce an undesirable result but can also be a reason for unpredicatability of a desired result.

BRIEF DESCRIPTION OF THE DRAWING

The FIGURE is a view of the anterior portion of a cornea with the various operative areas indicated.

BRIEF STATEMENT OF THE INVENTION

It is an object of the invention to provide improved procedure, before performing sculpturing laser surgery of the character indicated, whereby the laser surgery per se may be performed on a patient's cornea with greater confidence and assurance of achieving a given prescribed optically improved result.

Another object of the invention is to achieve the above result with improved post-operative procedure which favors smooth and sufficient epithelium regrowth over the surgically affected region of the cornea.

Still another object is to achieve the foregoing objects with procedural steps which are within existing skills of the ophthalmic surgeon and which use materials with which such surgeons are familiar.

The invention achieves these objects by performing the preoperative step of reoving the epithelial layer from a central area of the cornea, wherein such removed area is slightly greater than the area to be subjected to ablation under ultraviolet laser radiation, whereby such laser action is directed to an epithelium-free area, for immediate traversal of Bowman's membrane and penetration of the stroma. Precaution is taken to avoid deleterious dehydration effects in the thus-exposed area, and the laser-sculpting procedure is accomplished, generally to a maximum penetration depth of less than 40 microns, and within 30 to 40 seconds. Post-operative procedure favorable to smooth and efficient epitheleal regrowth over the surgically sculptured region is also described.

DETAILED DESCRIPTION

The invention will be described in detail in connection with the accompanying drawing which, on an enlarged scale, is a schematic view in front elevation of the anterior aspect of a cornea, with markings to permit descriptive identification of different significant areas involved in use of the invention.

As generally indicated above, the invention is concerned with extra-operative procedural steps, i.e., beyond the particular ultraviolet-irradiation procedure relied upon to selectively ablate the anterior surface of the cornea, with penetration into the stroma, whereby to achieve such volumetric removal of corneal tissue as to correctively change an optically deficient pre-existing curvature to an optically improved new curvature. Illustrative description of such deficiencies and different techniques for their corrective improvement through selective irradiation from an ultraviolet laser, such as an argon-fluoride excimer laser, will be found in the above-noted pending patent applications and in those prior patent applications to which the pending applications bear a continuing or continuation-in-part relation; reference may therefore be had to said applications for detailed description.

Important to the method of the present invention is the procedural step wherein epithelial-layer material is so locally removed from the anterior surface of the cornea as to assure no ultraviolet irradiation of the epithelium. For such assurance, this procedural step contemplates that epithelial-layer removal shall be throughout an area which continuously overlaps and surrounds the cornea-sculpting area of selective ablation via ultraviolet irradiation. If it is assumed that the cornea-sculpting area is a circle of 5 or 6-mm diameter, as could well be the case (a) for spherical-curvature reduction (to reduce a myopia condition) or (b) for spherical-curvature increase (to reduce a hyperopia condition) or (c) for cylindrical-curvature reduction (to reduce an astigmatism condition), then the area of epithelial-layer removal should be a circle which fully laps the cornea-sculpting area, preferably with a circumferentially continuous margin of about 1-mm incremental radius outside the circle of cornea-sculpting ablation. In the drawing, the circle 10 of cornea-sculpting action is seen in the central optically used portion of a cornea 11, and a preferred circle 12 of epithelial-layer removal is seen to be concentric with circle 10, thus providing a margin 13 of incremental radius outside circle 10, whereby to assure against epithelium exposure to ultraviolet irradiation.

Preferred pre-operative (i.e., pre-surgery) procedural steps, in the illustrative context of circular areas delineated above and in the drawing, will appear from the following recital of specific steps and precautions which I have taken in laser-sculpting operation upon human patients to date:

1. With the patient lying on his back, with his head restrained to face straight up, and with retractors set to hold back upper and lower eyelids, a peri-bulbar or retro-bulbar anesthetic is administered to obtain anesthesia of the anterior portion of the eye and relative akinesia of the extra-ocular muscles. 2. A suction device or other means for outer-annulus steadying contact with the eye is applied to an area 14 having substantial radial offset from the area 12 within which epithelium is to be removed.

3. Within the inner limit of the area 14 of eye-steadying contact, the epithelium is kept in normally moist condition, by application to the cornea of one or more drops of an isotonic solution.

4. Having selected a scraping tool, such as a molded plastic spatula-like implement having a relatively narrow blade, e.g., having a 2 to 3-mm wide scraping edge of moderate sharpness, proceed to dislodge only epithelial-layer material from within the circle 12, the dislodged material being pushed to and temporarily accumulated upon the remaining undisturbed epithelial layer, namely, within the annular area outside circle 12 and within the inner limit of the area 14 of fixation contact.

5. The scraping dislodgement of epithelium may or may not be totally effective with the indicated scraper, but if more moisture is needed to wash away all epithelial material within area 12, another drop of the isotonic solution can be applied, and a dry cotton-tipped tooth pick (e.g., a so-called "Q-Tip") may be employed to sweep area 12 clear of all epithelial material, thus exposing a clean and smooth anterior aspect of Bowman's membrane, within area 12. The same or another "Q-Tip" device is then used to pick up and discard all of the accumulation of scraped epithelial material, from the outer annulus, i.e., from the area around circle 12. At all stages of performing steps 4 and 5, extreme caution is needed to assure against any scratching or other mechanical invasion of Bowman's membrane.

6. The patient is now conditioned for one of the laser-sculpting procedures selected from said pending patent applications, it being understood that prior to any of the above-described pre-surgery steps, the laser-delivery surgical apparatus will have been brought to a condition of instant readiness to perform a predetermined control of ultraviolet irradiation within the laser-sculpting area 10. Generally speaking, the laser-sculpting operation begins immediately after completion of epithelium removal, and when the area of circle 12 is smoothly denuded and epithelium-free; laser sculpting proceeds to completion within one minute, and often less, e.g., about 30 seconds for a two-diopter spherical change of curvature; also generally speaking, the depth of penetration into the stroma will be less than 50 microns, e.g., about 20 microns for a two-diopter spherical change of curvature.

7. Immediately upon termination of the laser surgery of step 6 above, the speculum or other eye-contacting retainer means is removed, and a solution significantly containing a cycloplegic agent is applied, as by one or more drops of the solution, to the area of surgical operation, to temporarily paralyze ciliary and iris musculature, thereby preventing spasm, irritation or other patient discomfort; and an antibiotic ointment, such as an erythromycin or chloromycetin ointment is applied to environmentally protect and cover the entire exposed area of the cornea.

8. The lids are then released and taped in closed condition, and a moderate-pressure bandage is applied over the taped lids, the bandage being configured so as not to allow the lids to separate.

9. The patient is then given a quiescent post-operative recuperative period of rest, for enhanced opportunity of epithelium regrowth into smooth and total coverage of the anterior surface of the cornea. Generally speaking, this epithelium regrowth proceeds to substantial completion in about 48 hours. But bandage removal and replacement, at 11 to 12-hour post-surgery intervals, is recommended, in order to track the expected progress of epithelium regrowth. The patient is released upon the surgeon's judgment that epithelium regrowth is complete.

In my surgical experience to date, involving use of one or more inventions of above-identified patent applications, I have used special apparatus designed and constructed by Taunton Technolgies Inc., of Monroe, Conn. Said special apparatus is the subject of pending patent applications, Ser. No. 938,633, filed Dec. 5, 1986 and Ser. No. 009,724 filed Feb. 2, 1987, as well as apparatus-divisional applications based on disclosures of one or more of the patent applications first identified above.

What is claimed is:

1. The method of changing optical properties of an eye by operating solely upon the optically used area of the anterior surface of the cornea of an eye, which comprises the preliminary step of removing only the epithelial layer from said area, whereby within said area the cornea is epithelium-free, then within said area subjecting the cornea to selective tissue-ablating laser irradiation to selectively ablate the anterior surface of the cornea in a volumetric removal of corneal tissue and with depth penetration into the stroma to achieve a predetermined corneal profile, applying an environmentally protective cover to said area and adjacent epithelium, and affording a quiescent post-operative period for epithelium regrowth over said area.

2. The method of changing the anterior surface of the cornea of an eye from an initial curvature in an optically used area having defective optical properties to a subsequent curvature having correctively improved optical properties within said optically used area, which method comprises the preliminary step of removing only the epithelial layer from said area, whereby within said area Bowman's membrane is the externally exposed anterior surface of the cornea, then directionally and within said area impacting said externally exposed surface with tissue-ablating laser irradiation to selectively ablate the anterior surface of the cornea with penetration into the stroma and with volumetric sculpturing removal of corneal tissue to such penetration depth and profile as to characterize the anterior surface of the cornea with said subsequent curvature, applying an environmentally protective cover to said area and adjacent epithelium, and affording a quiescent post-operative period for epithelium regrowth over said area.

3. The method of changing optical properties of an eye by operating solely upon the optically used area of the anterior surface of the cornea of an eye, which comprises the preliminary step of removing only the epithelial layer from said area, whereby within said area the cornea is epithelium-free, then within said area subjecting the cornea to selective ultraviolet irradiation and attendant ablative photodecomposition in a volumetric removal of corneal tissue and with depth penetration into the stroma to achieve a predetermined corneal profile, applying an environmentally protective cover to said area and adjacent epithelium, and affording a quiescent post-operative period for epithelium regrowth over said area.

4. The method of changing the anterior surface of the cornea of an eye from an initial curvature in an optically used area having defective optical properties to a subsequent curvature having correctively improved optical properties within said optically used area, which method comprises the preliminary step of removing only the epithelial layer from said area, whereby within said area Bowman's membrane is the externally exposed anterior surface of the cornea, then directionally and within said area impacting said externally exposed surface with ultraviolet irradiation to selectively ablate the anterior surface of the cornea by photodecomposition with penetration into the stroma and with volumetric sculpturing removal of corneal tissue to such penetration depth and profile as to characterize the anterior surface of the cornea with said subsequent curvature, applying an environmentally protective cover to said area and adjacent epithelium, and affording a quiescent post-operative period for epithelium regrowth over said area.

5. The method of claim 4 or claim 3, claim 2 or claim 1, in which the area of epithelium-layer removal has peripherally continuous overlap with and is thus at least incrementally greater than the corneal area of irradiation exposure.

6. The method of claim 4 or claim 3, or claim 2 or claim 1 in which the irradiation exposure is for a period of one minute or less.

7. The method of claim 4 or claim 3, or claim 2 or claim 1 in which the irradiation exposure is such as to develop anterior-surface curvature correction with depth penetration of 50 microns or less.

8. The method of claim 4 or claim 3, or claim 2 or claim 1 in which the anterior surface of the cornea is moistened with one or more drops of an isotonic solution prior to epithelial-layer removal.

9. The method of claim 4 or claim 3, or claim 2 or claim 1 in which epithelial-layer removal is via gentle mechanical scraping.

10. The method of claim 4 or claim 3, or claim 2 or claim 1 in which epithelial-layer removal is via gentle scraping, dislodged epithelium being pushed out of said area so as to accumulate upon unscraped epithelium outside said area, the accumulation of dislodged epithelium being removed after said area has become epithelium-free.

11. The method of claim 4 or claim 3, or claim 2 or claim 1 in which epithelial-layer removal is via gentle scraping, dislodged epithelium being pushed out of said area so as to accumulate upon unscraped epithelium outside said area, washing said area with at least a drop of isotonic solution to assure total epithelium removal from said area, and removing the dislodged accumulation prior to irradiation.

12. The method of claim 4 or claim 3, or claim 2 or claim 1 in which an annular eye retainer is applied to the cornea for pre-operative eye fixation, the annulus of cornea contact being in radially outer surrounding offset from said area.

13. The method of claim 4 or claim 3, or claim 2 or claim 1 in which an annular eye retainer is applied to the cornea for pre-operative eye fixation, the annulus of cornea contact being in radially outer surrounding offset from said area, and the eye retainer being applied to the cornea prior to epithelium-layer removal from said area.

14. The method of claim 4 or claim 3, or claim 2 or claim 1 in which the area of irradiation is circular and in which the area of epithelial-layer removal is of at least one-millimeter radial extent greater than the area of ultraviolet-irradiation exposure.

15. The method of claim 4 or claim 3, or claim 2 or claim 1 in which at termination of irradiation exposure, a solution significantly containing a cycloplegic agent is applied to said area, whereby to temporarily paralyze ciliary and iris musculature of the eye.

16. The method of claim 4 or claim 3, or claim 2 or claim 1 in which at termination of irradiation exposure, a solution significantly containing a cycloplegic agent is applied to said area, whereby to temporarily paralyze ciliary and iris musculature of the eye, and then applying said cover in the form of an application of antibiotic ointment to said area, followed by taping the involved eyelids in closed condition.

17. The method of claim 4 or claim 3, or claim 2 or claim 1 in which at termination of irradiation exposure, a solution significantly containing a cycloplegic agent is applied to said area, whereby to temporarily paralyze ciliary and iris musculature of the eye, then applying said cover in the form of an application of antibiotic ointment to said area, followed by taping the involved eyelids in closed condition, and applying a moderate-pressure bandage configured so as not to allow the taped lid to separate.

18. The method of claim 4 or claim 3, or claim 2 or claim 1 in which in preparation for epithelium-layer removal of peri-bulbar or retro-bulbar anesthetic is administered to obtain anesthesia of the anterior portion of the eye and relative akinesia of involved extra-ocular musculature.

19. The method of claim 4 or claim 3, or claim 2 or claim 1 in which in preparation for epithelium-layer removal a peri-bulbar or retro-bulbar anesthetic is administered to obtain anesthesia of the anterior portion of the eye and relative akinesia of involved extra-ocular musculature, and then applying an annular eye retainer to the cornea for pre-operative eye fixation, the annulus of cornea contact being in radially outer surrounding offset from said area.

* * * * *

Notice of Adverse Decision in Interference

In Interference No. 102,073, involving Patent No. 4,770,172, F. A. L'Esperance Jr., METHOD OF LASER-SCULPTURE OF THE OPTICALLY USED PORTION OF THE CORNEA, final judgement adverse to the patentee was rendered Jan. 10, 1991, as to claims 1-19.

*(Official Gazette March 5, 1991)*